(12) United States Patent
Dowling

(10) Patent No.: US 7,722,639 B2
(45) Date of Patent: May 25, 2010

(54) SURGICAL RETRACTION DEVICE FOR REMOVAL OF SMALL ORGANS

(76) Inventor: Brian T. Dowling, P.O. Box 611, Elma, WA (US) 98541

( * ) Notice: Subject to any disclaimer, the term of this patent is extended or adjusted under 35 U.S.C. 154(b) by 122 days.

(21) Appl. No.: 11/671,348

(22) Filed: Feb. 5, 2007

(65) Prior Publication Data

US 2007/0191882 A1    Aug. 16, 2007

Related U.S. Application Data

(63) Continuation-in-part of application No. 11/217,689, filed on Aug. 31, 2005.

(60) Provisional application No. 60/608,307, filed on Sep. 9, 2004.

(51) Int. Cl.
*A61B 17/28* (2006.01)

(52) U.S. Cl. ........................................ 606/205; 606/208

(58) Field of Classification Search ................. 606/135, 606/151, 205–208; 600/231, 234–235, 227–229, 600/218; 604/104, 93.01; 26/99–100, 208, 26/211; 269/53–54, 54.1–54.5
See application file for complete search history.

(56) References Cited

U.S. PATENT DOCUMENTS

| | | | | |
|---|---|---|---|---|
| 2,070,670 A | * | 2/1937 | Marshall | 600/218 |
| 2,108,325 A | * | 2/1938 | Ziegler | 606/120 |
| 2,693,795 A | * | 11/1954 | Grieshaber | 600/213 |
| 2,704,399 A | * | 3/1955 | Melcher | 30/266 |
| 2,850,008 A | * | 9/1958 | Resch | 600/232 |
| 3,035,582 A | * | 5/1962 | Seiger | 606/205 |
| 3,168,093 A | * | 2/1965 | Gauthier | 600/232 |
| 3,752,152 A | * | 8/1973 | Kern | 600/218 |
| 4,344,420 A | * | 8/1982 | Forder | 600/232 |
| 4,867,139 A | * | 9/1989 | Girzadas | 600/210 |
| 6,083,240 A | * | 7/2000 | Ouchi | 606/205 |
| 6,558,392 B1 | * | 5/2003 | Martini | 606/90 |

FOREIGN PATENT DOCUMENTS

| | | | |
|---|---|---|---|
| GB | 232890 A | * | 10/1998 |
| JP | 2002095664 A | * | 4/2002 |

* cited by examiner

*Primary Examiner*—(Jackie) Tan-Uyen T. Ho
*Assistant Examiner*—Mark Mashack
(74) *Attorney, Agent, or Firm*—Seed IP Law Group PLLC

(57) ABSTRACT

A surgical device and tool for use in stabilizing tissue, such as an organ relative to a clamp, the surgical device having an elongate rigid member with a proximal end of the device having a stabilizing structure that rests against the skin of the subject and includes a vessel guide for guiding a blood vessel attached to the organ or tissue, and a tapered distal end that mounts on the clamp. The surgical tool includes the combination of a clamp and the above-mentioned surgical device, with the clamp having a hinge pin with tapered socket that receives mounted the distal end of the device and a flap positioned on the proximal end. The tool is used to stabilize an organ by placement of the stabilizing structure against the skin of the subject, guiding a blood vessel with the vessel hook, using the flap to hold tissue away from the organ, and clamping such vessel distal to the vessel guide. A ligature is then placed across the vessel between the vessel guide and the clamp.

12 Claims, 5 Drawing Sheets

SURGICAL RETRACTION DEVICE FOR REMOVAL OF SMALL ORGANS

BACKGROUND OF THE INVENTION

1. Field of the Invention

The present invention generally relates to the surgical removal of small organs and, more specifically, to an apparatus for the stabilization of tissue or an organ during a surgical procedure.

2. Description of the Related Art

Domesticated household pets such as dogs and cats are often spayed. The spaying of pet has many advantages. For example, a spayed pet is likely to have fewer incidences of certain medical problems, be more affectionate companions, and will not contribute to the problem of the production of unwanted litters. While the spaying of pets is a routine veterinary procedure, complications may nevertheless occur.

The spaying of a pet typically includes the steps of exteriorization of the ovaries and uterine horns, ligation of the ovarian pedicles, and transection of the ovarian pedicles distal to the ligature across the ovarian pedicles. During the ligation process, it is desirable to stabilize an ovary in an exteriorized position, as such exteriorization simplifies the placement of the ligature. However, as an ovary is under tension from the ovarian pedicle, traction is required to maintain the ovary in a stabilized exteriorized position.

Because the placement of the ligature requires two hands, the ligature across the ovarian pedicle may be placed while the ovary is exteriorized by either an assistant or by mechanical means.

Due to personnel cost, the spaying procedure is frequently completed by a veterinarian who is operating without the aid of an assistant. One typical solo technique of a spaying procedure requires the placement of a clamp on the ovarian pedicle, proximal to the intended ligature location, prior to the placement of the ovarian pedicle ligature. While the proximal clamp assists in the stabilization of the ovary in an exteriorized position, this method has many disadvantages. For example, the proximal clamp often crushes, and may even puncture the ovarian pedicle proximal to the ligature site. As the portion of the ovarian pedicle proximal to the transection site is not removed from the animal, such crushing or punctures may lead to blood loss or other surgical complications. Moreover, tissue associated with or near the organ, such as fat tissue, often interferes with access to the organ, visually and physically.

Another method of performing a solo spaying procedure involves the use of a Hauptman OHE Retractor (available from Jorgenson Laboratories of Loveland Colo.). A Hauptman OHE Retractor may be used to stabilize an ovary in an exteriorized position to aid in the placement of the ligature across the ovarian pedicle. However, a single size of a Hauptman OHE Retractor is only suitable for use on animals within a limited weight range. Further, it is prone to tipping over during the placement of the ovarian pedicle ligature, and the Hauptman OHE retractor is a complicated and costly device.

Therefore it is desirable to have a simple, stable, exteriorization device for use during a spaying procedure that does not require the clamping of the ovarian pedicle proximal to the ovarian pedicle ligature.

BRIEF SUMMARY OF THE INVENTION

The disclosed embodiments of the invention are directed to a surgical implement for the removal of organs, particularly with a clamp in removing reproductive organs from animals.

In accordance with one embodiment of the invention, a stabilizing device is provided that includes an elongated rigid member having a proximal end and a tapered distal end, the proximal end having a stabilizing structure configure to stabilize the organ, and the distal end having means adaptable to mount on a clamp.

In accordance with another embodiment of the invention, a surgical tool is provided that includes a clamp and a stabilizing device, the stabilizing device having an elongated rigid member with a proximal end and a distal end wherein the proximal end has a stabilizing structure configure to stabilize an organ and the distal end is adaptable to mount on a clamp. Ideally the clamp includes a hinge pin or pivot member configured to receive the tapered distal end of the elongated rigid member.

In accordance with another embodiment of the invention, the distal end is configured for slidable engagement in a socket formed on the clamp. Ideally, the distal end is straight and has a circular cross-sectional configuration that reduces in diameter towards the terminal end of the distal end, and the proximal end is a hook that depends from the distal end.

In accordance with another aspect of the foregoing embodiment, the hook includes a first curve having an arc in the range of 100° to 160° and a first radius, and a second curve following the first curve in an opposite direction having an arc in the range of approximately 100° to 160° and a second radius that is larger than the first radius. Ideally, the terminal end of the hook is straight and a flap or fence depends from the second curve.

In accordance with another aspect of the foregoing embodiment, the hook lies in a plane that is an angle to the longitudinal axis of the distal end, with the angle being an acute angle in the range of 5° to 45° or in the range of 15° to 30°.

In accordance with another embodiment of the invention, a tool is provided that includes a clamp; and a stabilizing device configured to be mounted on a hinge pin for the clamp, the stabilizing device including an elongate rigid member having a proximal end and a tapered distal end, the proximal end having a stabilizing structure configured to stabilize the organ relative to the clamp.

In accordance with another embodiment of the invention, a tool is provided that includes a unitary elongate member having a first section configured for slidable engagement in a socket formed on a hinge pin; a second section following the first section configured as a vessel guide; a third section following the second section configured as a stabilizing platform; and a guard or flap depending from the third section.

In accordance with another aspect of the foregoing embodiment, the hinge pin is straight and has a circular cross-sectional configuration with a tapered socket formed therein. While the remainder of the tool may also have a circular cross-sectional configuration, it is not absolutely required for the tool and the socket, and other configurations may be used of known geometric shapes, including, but not limited to, square, oblong, oval, elliptical, rectangular, etc. Ideally the vessel guide is formed to have a first curve with an arc in the range of 100° to 160° and a first radius, and the stabilizing platform follows the vessel guide and is curved in an opposite direction than the vessel guide and has an arc in a range of 100° to 160° and a second radius that is larger than the first radius. Ideally a terminal end of this tool is straight.

In accordance with another aspect of the foregoing embodiment, the stabilizing platform and vessel guide lie in the same plane and this plane is formed at an angle to a longitudinal axis of the first section or hinge pin. Preferably this is an acute angle and can be in the range of 5° to 45° and more preferably in the range of 15° to 30°.

In accordance with another aspect of the foregoing embodiment, the tool also includes a clamp having a first clamp member and a second clamp member that are hingedly attached together via a hinge pin having a socket.

BRIEF DESCRIPTION OF THE SEVERAL VIEWS OF THE DRAWINGS

The foregoing and other aspects of the present invention will be better appreciated with reference to the following detailed description of the invention taken in conjunction with the accompanying drawings, wherein.

DETAILED DESCRIPTION OF THE INVENTION

Figure 1:
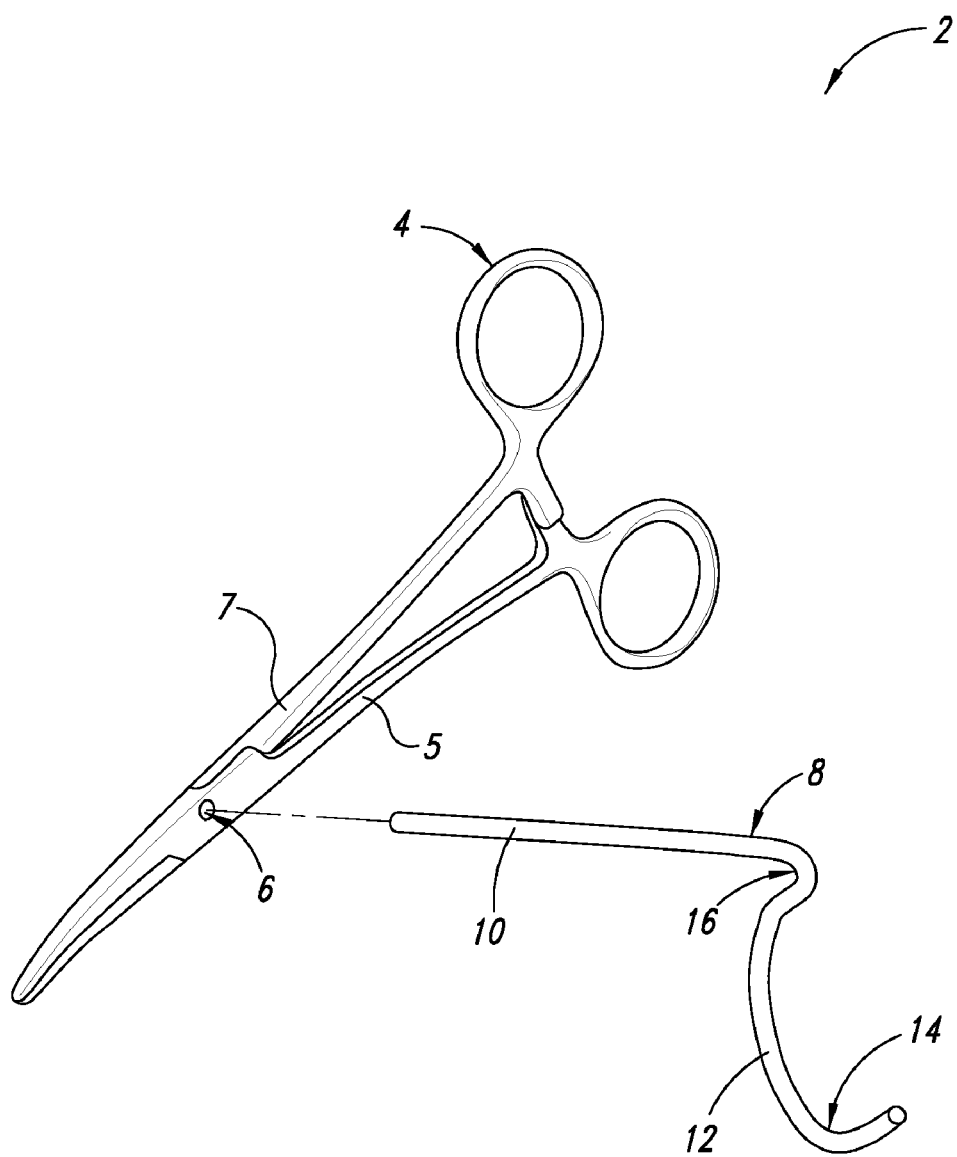
FIG. 1 is an exploded isometric view of a surgical tool of the present invention.

FIG. 1 is an exploded isometric view of a surgical tool of the present invention. The surgical tool 2 includes a clamp 4 and a stabilizing device in the form of an elongated rigid member 8. The clamp 4, as illustrated, is typical of the type that is used in the medical field and is readily commercially available. The clamp 4 has first and second clamp members 5, 7 pivotally connected together via a hinge pin (not shown) mounted via a hinge-pin hole 6 formed in each clamp member 5, 7. However, in the present invention, the hinge-pin has been omitted. Although FIG. 1 illustrates a particular type of clamp 4, one skilled in the art will appreciate that many other types of clamps and clamping devices may be used and adapted in accordance with the present invention.

The elongated rigid member 8 has a distal end 10 and a proximal end 12. The distal end 10 is configured to act as the hinge pin of clamp 4, via insertion into the hinge-pin hole 6. The diameter and shape of the distal end 10 and hinge-pin hole 6 is configured such that the elongate rigid member 8 does not rotate freely when clamp 4 is closed. Ideally, the distal end has a circular cross-sectional configuration and is straight, having a tubular or cylindrical shape and is formed of polished stainless steel. The distal end 10 is configured to allow the clamp 4 to slide along the distal end 10 and be detachable from the distal end 10. This configuration allows for use in a wider range of circumstances, ease of storage, and ease of decontamination.

Alternately, the distal end 10 may be configured to limit the range of motion upon which the clamp 4 can slide along the distal end 10. For example, features such as a bends, collars, or set screws may be attached to or formed on the distal end 10 of the elongated rigid member 8 to limit movement of the clamp 8 relative to the member 8. Such features not only limit the distance that the clamp 4 may slide along the distal end 10, but they may be placed such that the clamp 4 is fixedly mounted on the elongated rigid member 8 or cannot slide too close to the proximal end 12 of the elongated rigid member 8.

The proximal end 12 of the elongated rigid member 8 has a stabilizing platform 14 as well as a vessel guide 16. The stabilizing platform 14 is used to stabilize the tool, organ, and/or tissue against the skin or tissue of the patient. The vessel guide 16 is used to guide the blood vessel attached to the skin or tissue into the jaws of the clamp 4. The distal end 12 may contain different variations of stabilizing platforms 14. For example, the stabilizing platform 14 can have different sizes and shapes. The vessel guide 16 may contain bends of different sizes and shapes or even multiple bends. The size and shape of the vessel guide bend enables guiding of blood vessels of varying sizes and shapes into the jaws of the clamp 4. The terminal end of the distal guide is shown as straight, although it may be curved for particular applications.

Figure 3A:
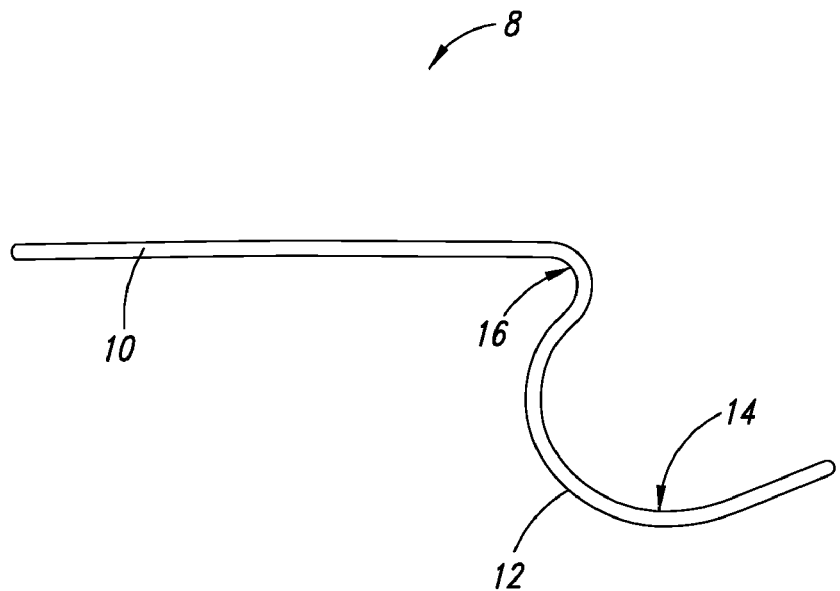
FIG. 3A is an isometric view of the stabilization member of the present invention.

In a preferred embodiment, the vessel guide 16 is arcuate, having a curved shape and depends from the straight distal end. As shown in FIG. 3A, it curves down and back toward the distal end with an arc in the range of 100° to 160° and, more preferably, in the range of 115° to 130°. In one embodiment it is 120°. The radius of the stabilizing platform 14 is in the range of 0.10 inch to 0.75 inch and, ideally is in the range of 0.20 inch to 0.375 inch. The radius of the vessel guide 16 is in the range of 1.0 inch to 2.0 inch and, in one embodiment, in the range of 1.15 inch to 1.5 inch. It is to be understood that radius of curvature and the arc for each of the stabilizing platform 14 and vessel guide 16 may be larger or smaller than the preferred ranges to accommodate different sizes of animals.

Figure 2:
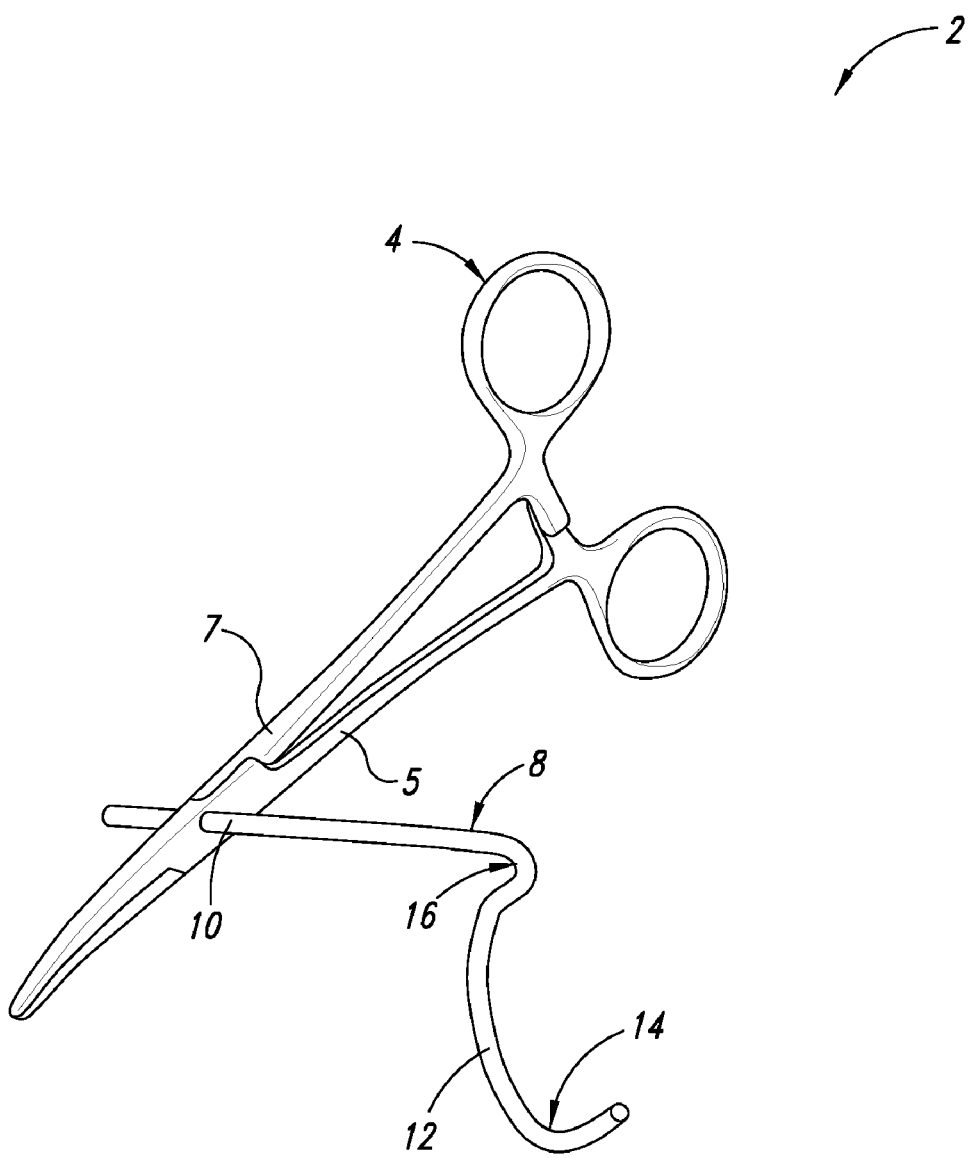
FIG. 2 is an isometric view of the assembled surgical tool of the present invention.

FIG. 2 is an isometric view of a preferred embodiment of the assembled surgical tool of the present invention. In this illustration, the distal end 10 of the elongated rigid member 8 is placed in the hinge-pin hole 6 of the clamp 4.

An exemplary use of the surgical tool is as follows: During a spaying procedure, an ovary and a uterine horn are first exteriorized. After exteriorization, the stabilization structure 14 is placed against the skin of the patient. The ovarian pedicle is placed into the vessel guide 16. A distal portion of the ovarian pedicle is clamped by the jaws of the clamp 4. After the clamping of the ovarian pedicle, the surgical tool 2 may rest against the subject's body. The veterinarian is then able to use both hands to place a ligature across the ovarian pedicle between the vessel guide 16 and the clamp 4. Such ligature may be placed distal to the vessel guide 16 and proximal to the jaws of the clamp 4. After placement of the ovarian pedicle ligature, the ovarian pedicle may be transected distal to the ligature. Due to the placement of the clamp 4 distal to the ligature site, the clamp 4 will not cause any damage proximal to the ligature.

FIG. 3A is an isometric view of a preferred embodiment of the stabilization member 8 of the present invention. As discussed above, the elongate rigid member 8 may have different sizes and shapes. For example, the size and shape of the stabilization platform 14 and the vessel guide 16 may be varied to accommodate organs of varying sizes and shapes. The distal end 10 may also include variations, such as the features discussed above, which limit the range upon which the clamp 4 may slide along the distal end 10.

Figure 3B:
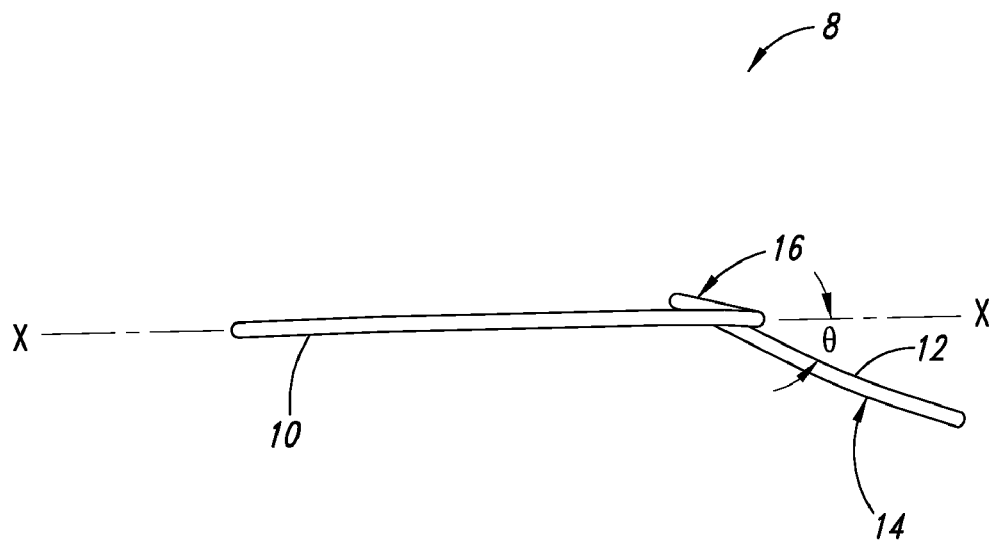
FIG. 3B is a side view of the stabilization member of the present invention.

FIG. 3B is a side view of the preferred embodiment of the stabilization member of the present invention. As can be seen in this illustration, the stabilization platform 14 and the vessel guide 16 are placed at an angle θ from a longitudinal axis X of the distal end 10 of the elongated rigid member 8. Placement of the stabilization platform 14 and the vessel guide 16 at an angle from the distal end 10 provides better access to the ovarian pedicle during placement of the ligature. The ideal angle will vary depending on animal and organ on which the stabilization member is to be used. However, an acute angle between 5° and 60° as shown in FIG. 4 should provide sufficient access. Preferably the angle θ is in the range of 15° to 45° and, more preferably at 30°, although this angle can vary according to personal preference and the size of the animal.

Figure 4A:
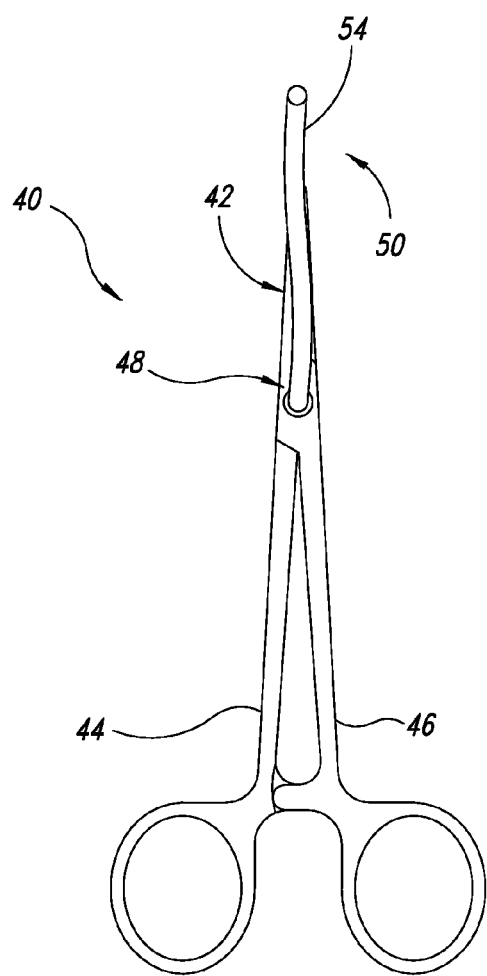
FIGS. 4A and 4B are top and side views respectively of a surgical tool formed in accordance with another embodiment of the invention.
Figure 4B:
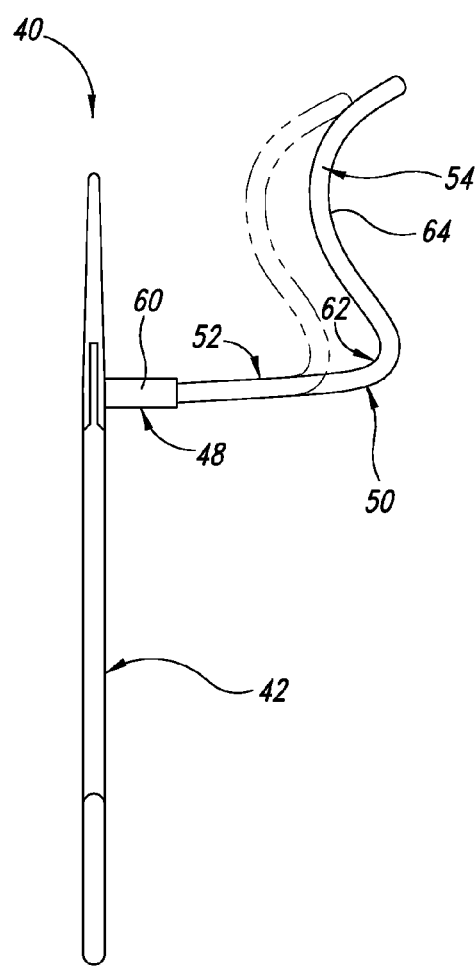

An alternative embodiment of the present disclosure is shown in FIGS. 4A-4B in which a surgical tool 40 is shown to include a manually-operated clamp 42 having first and second clamp members 44, 46 pivotally mounted together via a hinge pin 48. Ideally, the hinge pin 48 is permanently attached to the clamp 42 so that it cannot be removed. However, other attaching means can be utilized that allow the hinge pin 48 to be removed from the mounting holes in the first and second clamp members 44, 46.

The surgical tool 40 further includes a stabilization tool 50 engaged with the hinge pin 48. The stabilizing tool 50 includes a distal end 52 and proximal end 54 having a similar configuration as the stabilizing tool 8 shown in FIG. 1 with several differences. First, the distal end 52 has a tapered terminal end 56 that tapers in its diameter to be slidably received within a tapered axial bore 58 formed in a socket 60 with the hinge pin 48. Thus, the hinge pin 48 includes the socket 60 that extends from the clamp 42, and the longitudinal axial bore 58 in the socket 60 is tapered to match the taper of the terminal end 56 of the stabilizing tool 50. In one embodiment, a morse taper is used. It is to be understood that other tapers may be used for slidably engaging the stabilizing tool 50 with the socket 60. The hinge pin 48 also includes a pin member (not shown) that is mounted to the first and second clamp members 44, 46, preferably with permanent attachment to the clamp member on the opposite side of the socket 60 to permit rotation of the other clamp member as described above. The slidable engagement of the stabilizing tool 50 with the hinge pin 48 permits selective orientation of the stabilizing tool 50 relative to the clamp 42 to accommodate different surgical situations.

In this embodiment, the surgical tool 50 includes the first curve 62 and second curve 64 as described above with respect to the first embodiment depicted in FIG. 1. However, in the embodiment shown in FIG. 5, a flap 66 is shown depending from the second curve 64 of the stabilizing tool 50. This flap 66 serves as a guard or fence to hold tissue, such as fat tissue, away from the organ during the surgical procedure.

Figure 5:
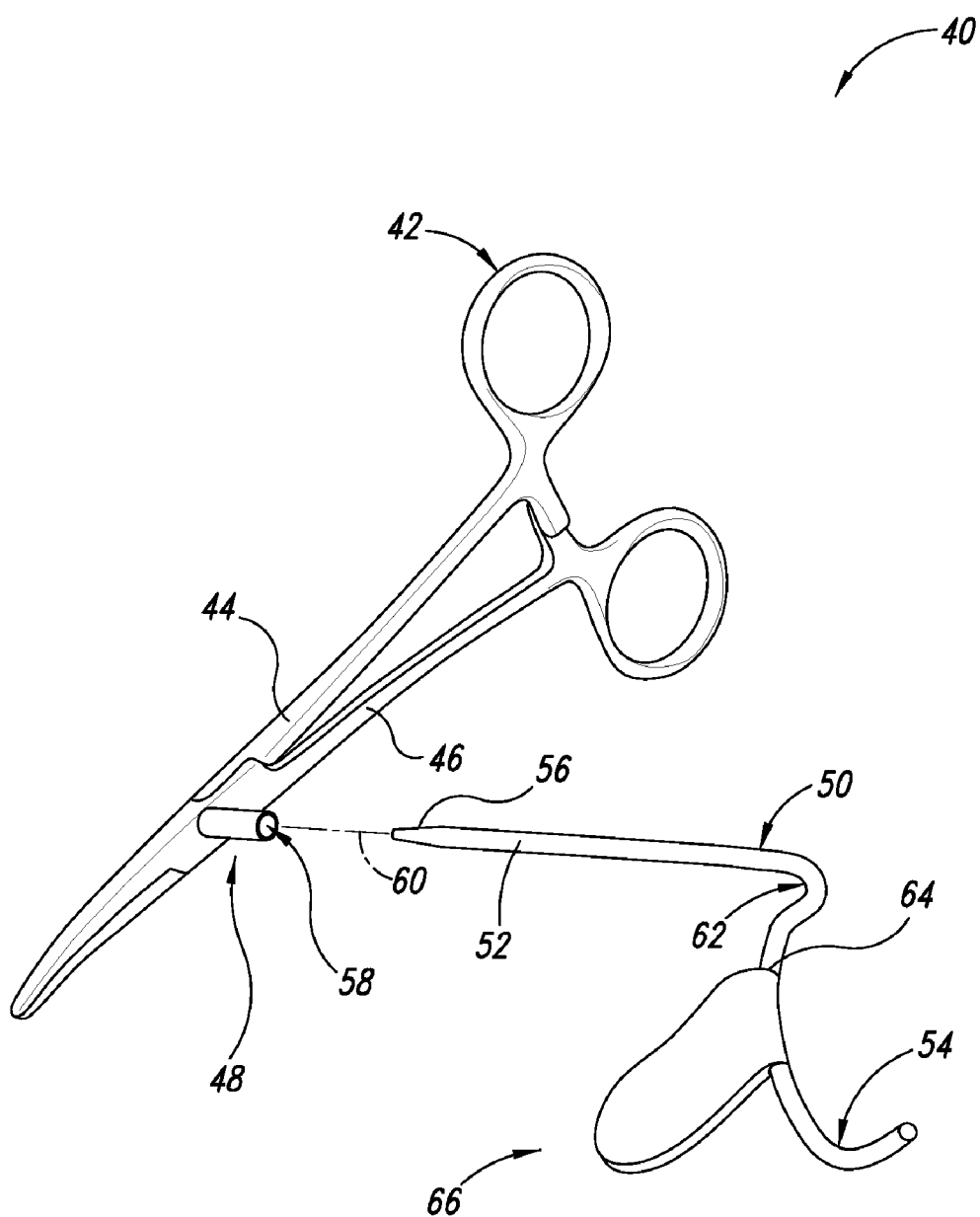
FIG. 5 is an exploded isometric view of the surgical tool of FIGS. 4A and 4B.

In the embodiment shown in FIG. 5, the flap 66 is curved, showing it can be formed of flexible or compliant material. In one embodiment this could be P strip material, such as silicone material, although it can be formed of stainless steel. It is important that the material be autoclavable and nontoxic. While a little flexibility is good, a rigid flap 66 can be used as well. The goal is to hold fat away from the ligature site.

Ideally, the flap 66 can slide on and off the stabilizing tool 50, although it can be integrally formed therewith, and this flap 66 can be used with all sizes of stabilizing tools 50.

In a preferred embodiment, the hinge pin 48 has a socket portion 60 that is in the length of 1 to 5 mm and preferably in the range of 3 to 4 mm. The length of the terminal end 56 of the stabilizing tool 50 that tapers is in the range of 6 mm to 10 mm, although a preferred range of 7 mm to 9 mm is used, and a preferred length of 8 mm can be used in most embodiments. The diameter of the tapered terminal end 56 ranges from 1 to 2 cm. In other words, the diameter tapers from approximately 2 cm down to 1 cm. However, it is to be understood that other diameters can be used.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A surgical device for stabilizing an organ, the device comprising: a clamp having first and second clamp members configured to be pivotally attached via a hinge pin hole formed in each of the first and second clamp members; an elongated one-piece rigid member having a proximal end and a tapered distal end, the proximal end comprising a hook member with a first curve and second curve, the first curve having an arc of approximately 100° to 160° with a first radius, the second curve following the first curve in an opposite direction having an arc of approximately 100° to 160° with a second radius that is larger than the first radius; a flap extending from the second curve; wherein the tapered distal end is configured to be inserted through the hinge pin holes of the first and second clamp members.

2. The device of claim 1 wherein the tapered distal end has a length in the range of 7 mm to 9 mm.

3. The device of claim 1 wherein the second curve has a terminal end that is straight.

4. The device of claim 1 wherein the proximal end lies in an plane that is at an acute angle to the longitudinal axis of the tapered distal end.

5. The device of claim 4 wherein the acute angle is in the range of 5° to 45°.

6. The device of claim 5 wherein the acute angle is in the range of 15° to 30°.

7. A surgical tool for use in stabilizing an organ and associated tissue comprising: a clamp configured to grip tissue, the clamp having a tapered longitudinal bore; a stabilizing device comprising an elongate rigid member having a proximal end and a tapered distal end, the proximal end comprising a hook member with a first curve and a second curve, first curve having an arc of approximately 100° to 160° with a first radius, the second curve following the first curve in an opposite direction having an arc of approximately 100° to 160° with a second radius that is larger than the first radius, the proximal end has a circular cross-sectional configuration, the distal end is straight and has a circular cross-sectional configuration; a fence extending from the proximal end and configured to hold the associated tissue away from the organ; wherein the tapered longitudinal bore is configured to receive the tapered distal end.

8. The device of claim 7 wherein the distal end is tapered for slidable engagement in the socket on the clamp.

9. The device of claim 7 wherein the second curve has a terminal end that is straight and fence extends from the second curve.

10. The device of claim 7 wherein the proximal end lies in an plane that is at an acute angle to a longitudinal axis of the tapered distal end.

11. The device of claim 10 wherein the acute angle is in the range of 5° to 45°.

12. The device of claim 11 wherein the acute angle is in the range of 15° to 30°.

* * * * *